(12) United States Patent
Möhlinger

(10) Patent No.: US 11,828,994 B2
(45) Date of Patent: Nov. 28, 2023

(54) COUPLING DEVICE FOR LIGHT GUIDES

(71) Applicant: Scholly Fiberoptic GmbH, Denzlingen (DE)

(72) Inventor: Eugen Möhlinger, Friesenheim (DE)

(73) Assignee: Schölly Fiberoptic GmbH, Denzlingen (DE)

(*) Notice: Subject to any disclaimer, the term of this patent is extended or adjusted under 35 U.S.C. 154(b) by 0 days.

(21) Appl. No.: 17/591,762

(22) Filed: Feb. 3, 2022

(65) Prior Publication Data
US 2022/0252804 A1   Aug. 11, 2022

(30) Foreign Application Priority Data
Feb. 8, 2021 (DE) .......................... 102021102887.6

(51) Int. Cl.
| | | |
|---|---|---|
| *H04B 10/00* | (2013.01) | |
| *G02B 6/42* | (2006.01) | |
| *G02B 23/24* | (2006.01) | |
| *A61B 1/07* | (2006.01) | |
| *A61B 1/00* | (2006.01) | |

(52) U.S. Cl.
CPC ......... *G02B 6/4296* (2013.01); *G02B 6/4292* (2013.01); *G02B 23/2469* (2013.01); *G02B 23/2476* (2013.01); *A61B 1/00126* (2013.01); *A61B 1/07* (2013.01); *G02B 2006/4297* (2013.01)

(58) Field of Classification Search
CPC .......................... G02B 6/4296; G02B 6/4292; G02B 23/2469; G02B 23/2476; G02B 2006/4297; G02B 6/0006; G02B 6/26; G02B 23/2461; A61B 1/00126; A61B 1/07
See application file for complete search history.

(56) References Cited

U.S. PATENT DOCUMENTS

| | | | | |
|---|---|---|---|---|
| 3,835,854 A * | 9/1974 | Jewett | ................ | A61M 25/0113 604/159 |
| 4,028,081 A * | 6/1977 | Marcatili | ............... | G02B 6/448 65/435 |
| 4,087,155 A * | 5/1978 | Deacon | ................ | G02B 6/3841 403/14 |
| 4,146,300 A * | 3/1979 | Kaiser | .................. | G02B 6/3843 385/72 |
| 4,158,476 A * | 6/1979 | McCartney | .......... | G02B 6/3841 385/82 |
| 4,181,402 A * | 1/1980 | Borsuk | ................ | G02B 6/3821 385/82 |
| 4,208,093 A * | 6/1980 | Borsuk | ................ | G02B 6/3841 385/87 |
| 4,279,468 A * | 7/1981 | Turley | ................ | G02B 6/3888 385/59 |

(Continued)

FOREIGN PATENT DOCUMENTS

DE   102016009840   7/2019

*Primary Examiner* — Agustin Bello
(74) *Attorney, Agent, or Firm* — Volpe Koenig

(57) ABSTRACT

A coupling device (9) for light guides (8), including a light entrance (11) and a light-guide space (12) aligned at the light entrance (11), and including a clamping device with a first roller pair (20) with two opposing rollers (21; 32), between which an inserted light guide (8) can be clamped. The coupling device (9) has a second roller pair (26) with two opposing rollers (21), and the second roller pair (26) is arranged closer to the light entrance (11) than the first roller pair (20).

16 Claims, 5 Drawing Sheets

(56) References Cited

U.S. PATENT DOCUMENTS

| | | | | |
|---|---|---|---|---|
| 4,302,072 A * | 11/1981 | Vucins | G02B 6/3881 | 385/48 |
| 4,378,145 A * | 3/1983 | Stancati | G02B 6/3841 | 385/64 |
| 4,383,532 A * | 5/1983 | Dickhudt | A61M 25/0113 | 607/117 |
| 4,389,091 A * | 6/1983 | Lidholt | G02B 6/3841 | 385/64 |
| 4,429,949 A * | 2/1984 | Cartier | G02B 6/3841 | 385/64 |
| 4,468,087 A * | 8/1984 | Milan | G02B 6/3841 | 385/74 |
| 4,490,006 A * | 12/1984 | Lidholt | G02B 6/3841 | 385/85 |
| 4,490,007 A * | 12/1984 | Murata | G02B 6/3882 | 385/80 |
| 4,616,648 A * | 10/1986 | Simpson | A61M 25/0113 | 606/108 |
| 4,746,194 A * | 5/1988 | Rasmussen | G02B 6/3841 | 385/80 |
| 4,767,177 A * | 8/1988 | Cartier | G02B 6/3843 | 385/81 |
| 4,807,957 A * | 2/1989 | de Jong | G02B 6/3882 | 385/60 |
| 4,856,354 A * | 8/1989 | Overbay | G02B 23/2476 | 73/866.5 |
| 5,346,498 A * | 9/1994 | Greelis | A61M 25/0119 | 606/108 |
| 5,389,100 A * | 2/1995 | Bacich | A61M 25/0119 | 606/108 |
| 5,586,968 A * | 12/1996 | Grundl | A61B 1/31 | 600/114 |
| 5,821,920 A * | 10/1998 | Rosenberg | G05B 19/409 | 345/161 |
| 6,077,219 A * | 6/2000 | Viebach | A61B 1/2736 | 600/114 |
| 6,171,234 B1 * | 1/2001 | White | A61M 25/09041 | 600/102 |
| 6,275,724 B1 * | 8/2001 | Dickinson | A61B 5/067 | 600/424 |
| 6,280,098 B1 * | 8/2001 | Alcock | G02B 6/3874 | 385/64 |
| 6,290,675 B1 * | 9/2001 | Vujanic | A61M 25/0113 | 604/164.13 |
| 6,447,447 B1 * | 9/2002 | Mitsumori | A61B 1/00188 | 600/129 |
| 6,470,302 B1 * | 10/2002 | Cunningham | G09B 23/30 | 434/262 |
| 7,134,795 B1 * | 11/2006 | Bonna | G02B 6/3843 | 385/85 |
| 7,175,635 B2 * | 2/2007 | Loser | A61B 17/3403 | 606/130 |
| 7,276,044 B2 * | 10/2007 | Ferry | A61B 34/71 | 604/95.01 |
| 7,603,159 B2 * | 10/2009 | Rasche | A61B 6/12 | 604/510 |
| 7,887,549 B2 * | 2/2011 | Wenderow | A61M 25/0147 | 600/585 |
| 8,114,032 B2 * | 2/2012 | Ferry | A61B 90/50 | 604/510 |
| 8,343,041 B2 * | 1/2013 | Byers | A61M 39/06 | 600/154 |
| 8,747,352 B1 * | 6/2014 | Lalonde | A61M 25/0147 | 604/95.04 |
| 9,458,049 B2 * | 10/2016 | Ortiz | B29D 11/00721 | |
| 9,782,564 B2 * | 10/2017 | Zirps | A61M 25/0116 | |
| 10,215,976 B2 * | 2/2019 | Klose | G02B 6/4226 | |
| 10,391,278 B2 * | 8/2019 | Schulz | A61M 25/0113 | |
| 10,406,321 B1 * | 9/2019 | Macy | A61M 25/01 | |
| 10,578,810 B2 * | 3/2020 | Watte | G02B 6/3866 | |
| 11,585,986 B2 * | 2/2023 | Corl | G02B 6/3874 | |
| 2007/0163302 A1 * | 7/2007 | Kemmochi | C03B 37/0126 | 65/435 |
| 2007/0250000 A1 * | 10/2007 | Magnin | A61B 8/4461 | 600/114 |
| 2010/0069833 A1 * | 3/2010 | Wenderow | A61M 25/0147 | 604/95.01 |
| 2011/0015484 A1 * | 1/2011 | Alvarez | A61B 34/30 | 604/528 |
| 2012/0179167 A1 * | 7/2012 | Wenderow | A61B 34/30 | 606/130 |
| 2013/0231678 A1 * | 9/2013 | Wenderow | A61B 34/30 | 606/130 |
| 2013/0274657 A1 * | 10/2013 | Zirps | A61M 25/09041 | 604/95.01 |
| 2014/0243642 A1 * | 8/2014 | Deac | A61B 18/1492 | 600/374 |
| 2014/0276233 A1 * | 9/2014 | Murphy | G01L 1/25 | 600/587 |
| 2014/0276948 A1 * | 9/2014 | Zirps | A61B 34/35 | 606/130 |
| 2015/0157196 A1 * | 6/2015 | Van Der Mark | A61B 1/00114 | 134/104.1 |
| 2015/0231287 A1 * | 8/2015 | Lin | A61M 25/0097 | 607/80 |
| 2015/0366435 A1 * | 12/2015 | Williams | A61M 25/0136 | 600/149 |
| 2016/0158437 A1 * | 6/2016 | Biasi | F04B 53/08 | 417/279 |
| 2017/0007098 A1 * | 1/2017 | Gora | G16H 30/20 | |
| 2018/0052317 A1 * | 2/2018 | Klose | G02B 6/4226 | |
| 2018/0214302 A1 * | 8/2018 | Dabrowiak | A61F 7/0085 | |
| 2018/0214303 A1 * | 8/2018 | Dabrowiak | A61F 7/0085 | |
| 2018/0338797 A1 * | 11/2018 | Moore | A61B 5/065 | |
| 2019/0133820 A1 * | 5/2019 | Jacobsen | A61F 7/0085 | |
| 2019/0154026 A1 * | 5/2019 | Kamen | G16H 40/67 | |
| 2019/0290888 A1 * | 9/2019 | Rochon | A61B 18/245 | |
| 2019/0313940 A1 * | 10/2019 | Thienphrapa | A61B 5/6852 | |
| 2020/0015717 A1 * | 1/2020 | Taghioskoui | H01J 49/0422 | |
| 2020/0038106 A1 * | 2/2020 | Pieper | A61B 34/30 | |
| 2020/0367968 A1 * | 11/2020 | Rochon | A61B 18/22 | |
| 2022/0111181 A1 * | 4/2022 | Hebert | A61M 25/09 | |
| 2022/0152349 A1 * | 5/2022 | Sowards | A61B 5/6852 | |
| 2022/0252804 A1 * | 8/2022 | Möhlinger | G02B 6/0006 | |

* cited by examiner

COUPLING DEVICE FOR LIGHT GUIDES

INCORPORATION BY REFERENCE

The following documents are incorporated herein by reference as if fully set forth: German Patent Application No. 10 2021 102 887.6, filed Feb. 8, 2021.

TECHNICAL FIELD

The invention relates to a coupling device for light guides, comprising a light entrance and a light-guide space aligned at the light entrance, and comprising a clamping device with a first roller pair with two opposing rollers, between which an inserted light guide can be clamped.

BACKGROUND

By way of example, such coupling devices are used in endoscopes to feed light from a light source into a light guide that leads to an endoscope.

In such coupling devices there is the risk of the light guide possibly slipping at a free end at the light entrance as a result of a lateral load on the light guide, and so the optimal position for the entry of light into the light guide is no longer maintained. As a result, the full luminous power is no longer available and light can reach into the light-guide space next to the light guide. This free light may emerge from the coupling device and may represent a risk to persons, particularly in the case of laser light.

SUMMARY

The invention considers the improvement of a coupling device of the aforementioned type.

According to the invention, this object is achieved by a coupling device having one or more of the features disclosed herein.

Accordingly, the coupling device according to the invention is characterized in that the coupling device has a second roller pair with two opposing rollers for clamping the light guide, the second roller pair being arranged closer to the light entrance than the first roller pair.

By way of the second roller pair the light guide is clamped a second time at a distance from the first instance of clamping. This mounting at two points of the light guide prevents a lateral load from bringing about a tilt or slip of the light guide in relation to the light entrance. Consequently, accurate positioning of the light guide is provided at all times.

The second roller pair can be arranged parallel to the first roller pair. In a preferred embodiment, however, the spindles of the rollers of the first roller pair and the spindles of the rollers of the second roller pair form an angle.

It is particularly preferable for the angle to be 90°. Tilting in all directions is prevented to the same extent in this way.

In an embodiment, the rollers of a roller pair have a rotationally symmetric form. In this way, a light guide can be introduced more easily into the coupling device.

In an embodiment, the rollers each have a guide, in particular a guide groove, for a light guide. The guide brings about additional fixation and centration in a plane perpendicular to the axis of rotation of the roller.

In an embodiment, the rollers of at least one roller pair, in particular of the second roller pair, are mounted eccentrically. Consequently, turning the rollers can cause the surface of the rollers to be moved closer to, or further away from, the light guide. This can bring about a fixation and a centration of the light guide.

In an embodiment, the rollers of at least one of the two roller pairs have a self-locking design. This can prevent independent release of the fixation.

Self-locking can be achieved, in particular, by virtue of the slope of an eccentric bearing being less than 7°. In this case, the slope can be measured as a dependence on the radius to a circumferential point. Accordingly, the slope is greater the further the rotational mount is away from the geometric axis of symmetry of the roller.

In an embodiment, the rollers of at least one roller pair, in particular of the first roller pair, are mounted centrically and are movable toward one another.

In particular, it is advantageous for the first roller pair to be mounted centrically and the second roller pair to be mounted eccentrically, or for both roller pairs to be mounted eccentrically.

In an embodiment, the coupling device has a guide, in particular a slotted guide, which moves the rollers of a roller pair away from the light guide. As a result, a clamped light guide can be released again.

In an embodiment, the guide has a holding position and is impinged by a spring which moves the guide from the holding position to an open position.

In an embodiment, the guide has an axially movable design, the axial movement of the guide bringing about a radial movement of the rollers. As a result, a compact and space-saving structure can be achieved.

In an embodiment, the coupling device has a rotary actuator and a converter, a rotational movement of the rotary actuator being converted into an axial movement of the slotted guide by the converter. A simple actuation of the slotted guide can be obtained in this way, and so fixation and release of a light guide is made easy. The rotary actuator may have a latching holding position, and so a release of a light guide during the use is prevented.

In an embodiment, the rollers of at least one of the two roller pairs have coupling of their rotational movement. This means the rotation of one roller is transferred to the other roller of the roller pair, preferably with an inverted sense of rotation. This can bring about uniform movement of the two rollers and ensure that these rollers have the same position in relation to the light guide. Particularly in the case of eccentrically mounted rollers, this can bring about improved centration of the light guide since the radius at the point of contact of the light guide to both rollers is the same.

In an embodiment, the rollers of at least one of the two roller pairs are braced against one another by a spring. This can bring about improved centration of the light guide. Additionally, the spring can bring about a holding force which, especially together with self-locking rollers, is capable of bringing about a fixation of the light guide.

Especially in the case of an eccentric mount, the rollers may have a flattening on the circumference, in particular on the side facing away from the light guide. This can simplify the structure and the assembly of the coupling device.

In a development of the invention, the coupling device has a deactivation device which prevents an entry of light into the light-guide space when no light guide has been inserted. By way of example, this can prevent persons from being blinded. This may prevent possible injuries to the eyes in the case of powerful light sources, in particular lasers.

In an embodiment, the deactivation device is designed to electrically deactivate a light source. This is the most reliable way of preventing blinding. For instance, the deactivation device may have a switch in this embodiment, the switch being actuated by an inserted light guide.

In an embodiment, the light guiding path is interruptible, the light entrance being capable of being sealed in light-tight fashion in particular. By way of example, this may be implemented by a stop or a movable cover which seals the light entrance of the coupling device and which is opened by a light guide.

BRIEF DESCRIPTION OF THE DRAWINGS

The invention is explained in more detail below on the basis of exemplary embodiments, with reference being made to the attached drawings, in which.

DETAILED DESCRIPTION

Figure 1:
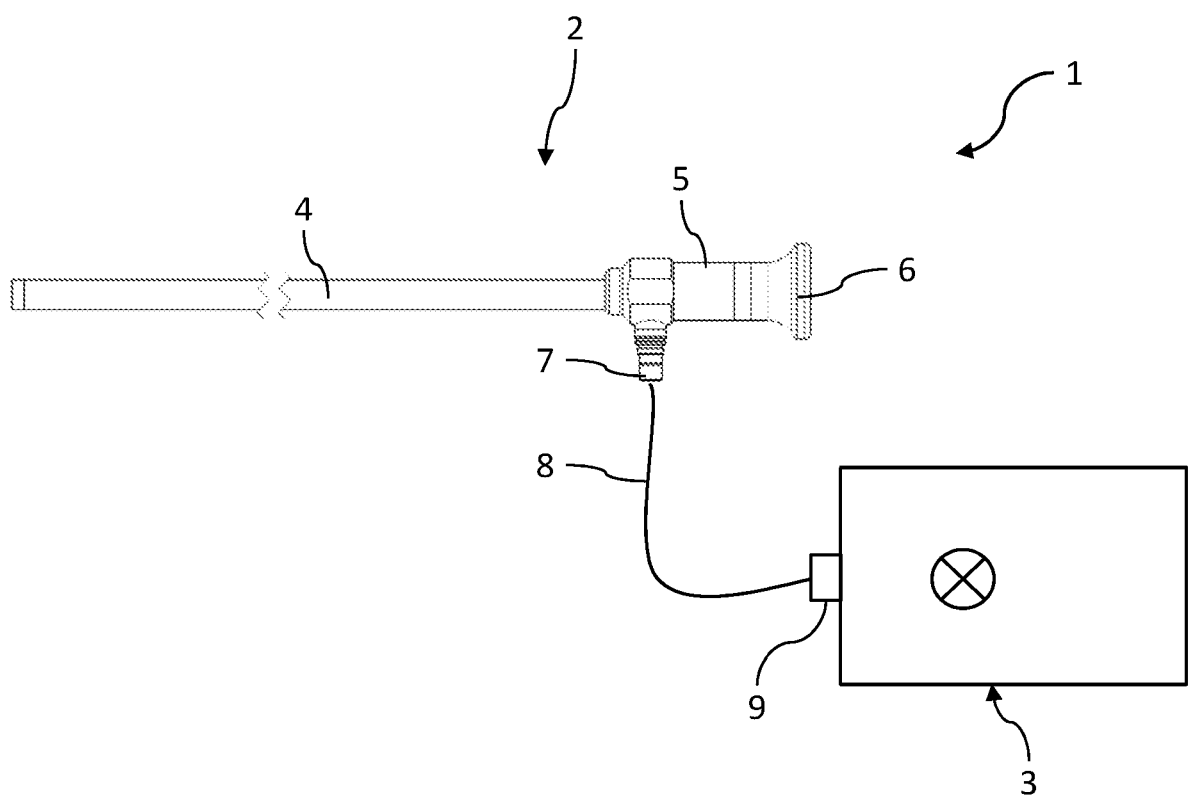
FIG. 1: shows a schematic block representation of an endoscope arrangement.
Figure 2:
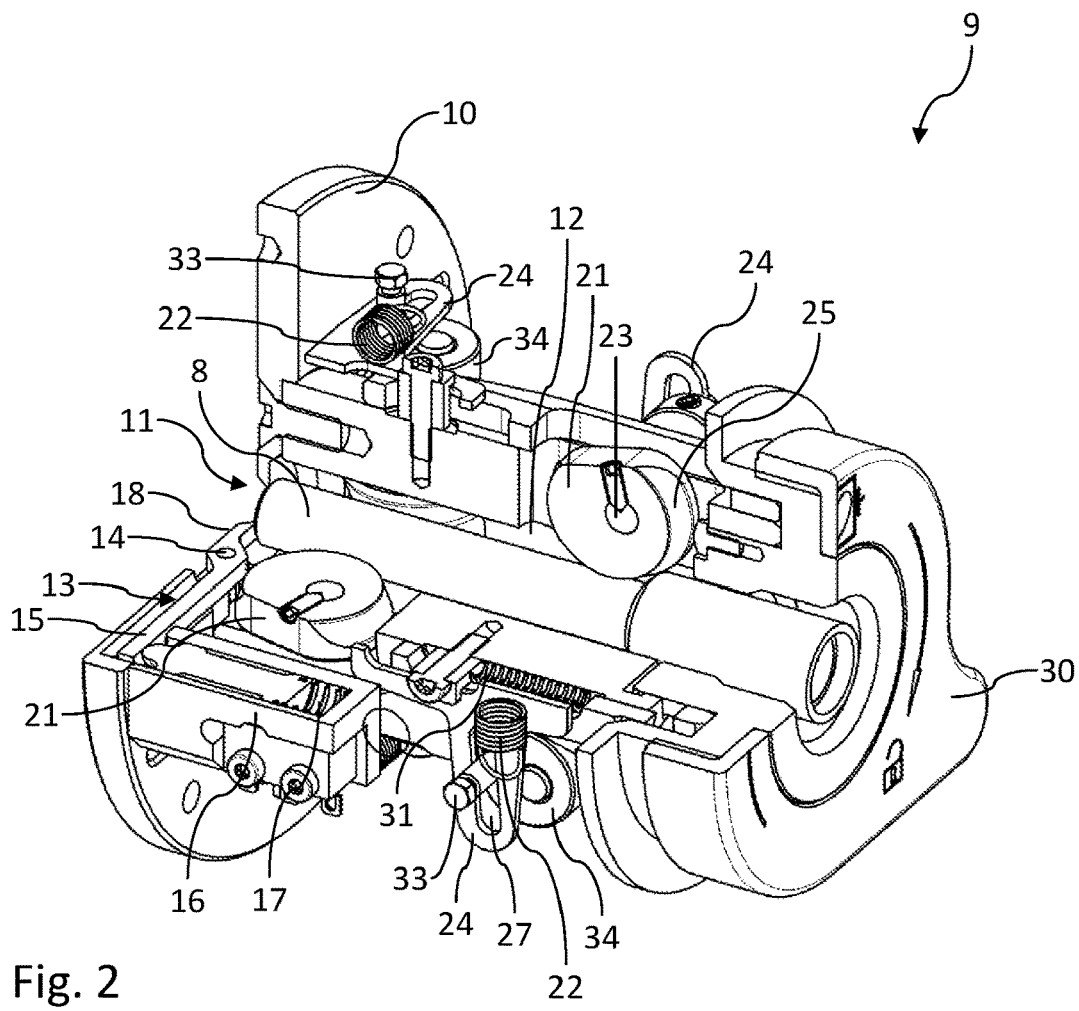
FIG. 2: shows a partial section of a coupling device with two eccentrically mounted roller pairs.
Figure 3:
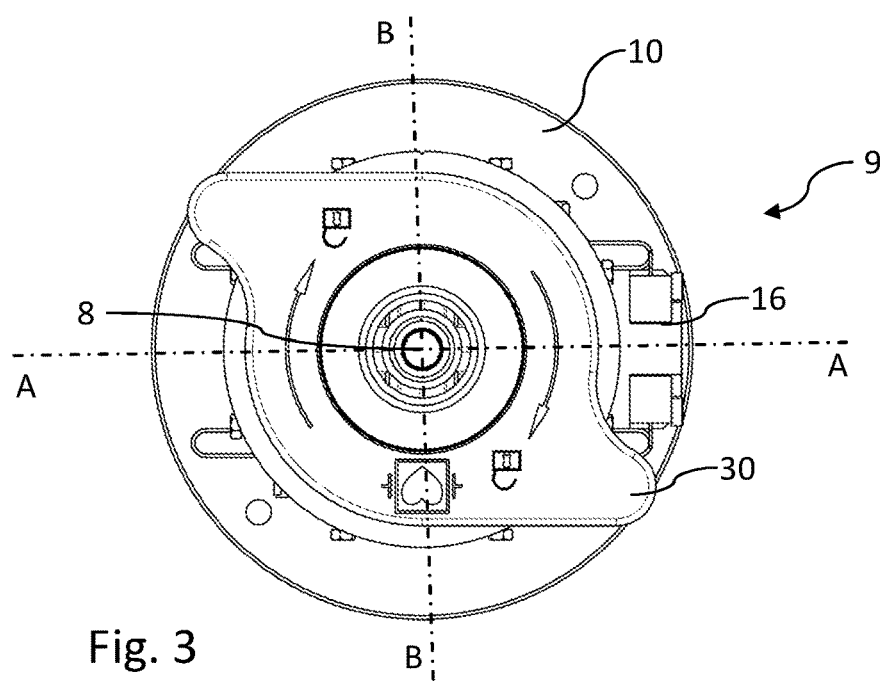
FIG. 3: shows a front view of the coupling device of FIG. 2, FIG. 4: shows a longitudinal section of the coupling device of FIG. 2 along the line A-A in FIG. 3, FIG. 5: shows a longitudinal section of the coupling device of FIG. 2 along the line B-B in FIG. 3, FIG. 6: shows a partial section of a coupling device with one eccentrically mounted roller pair and one centrically and radially movably mounted roller pair.
Figure 4:
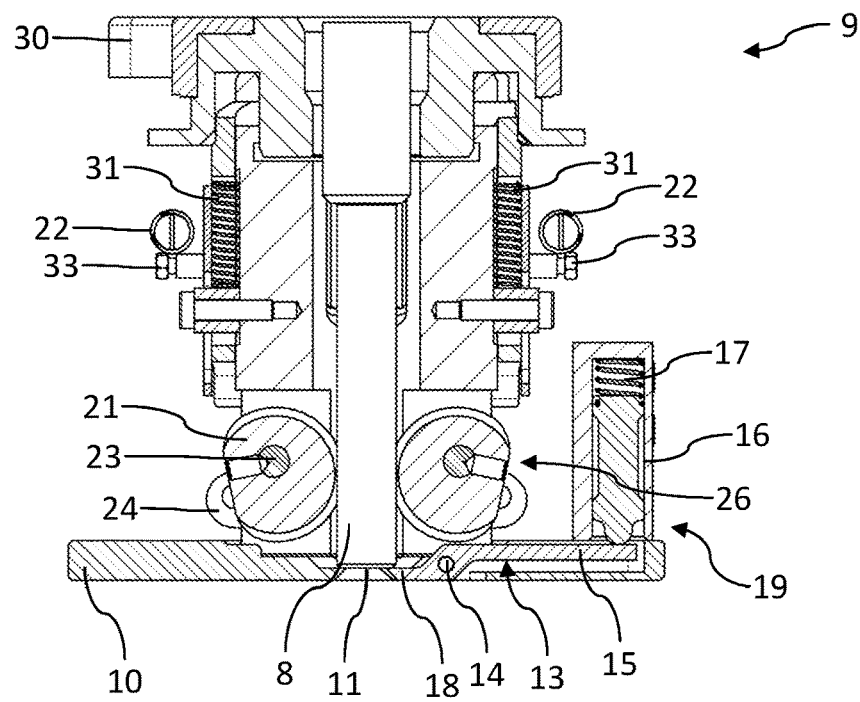
Figure 5:
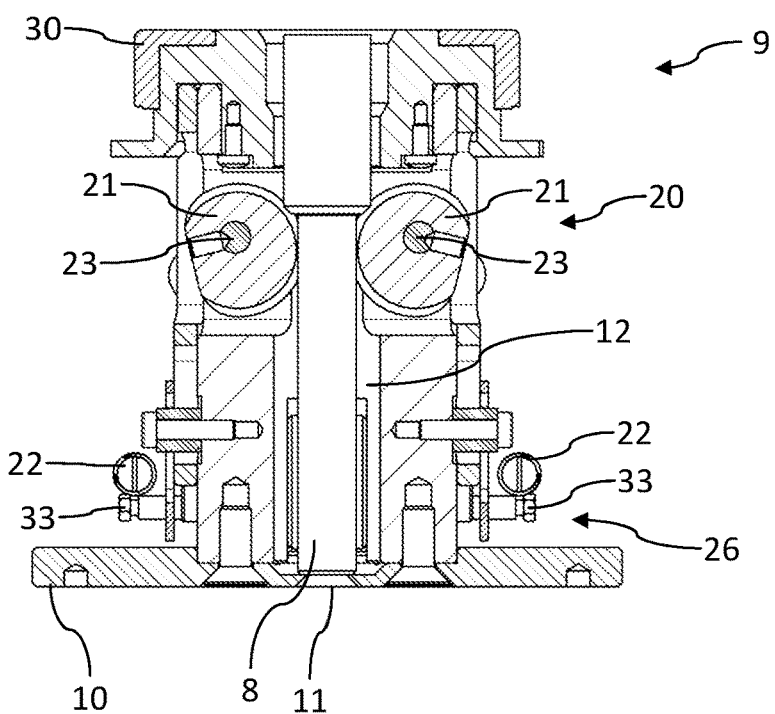
Figure 6:
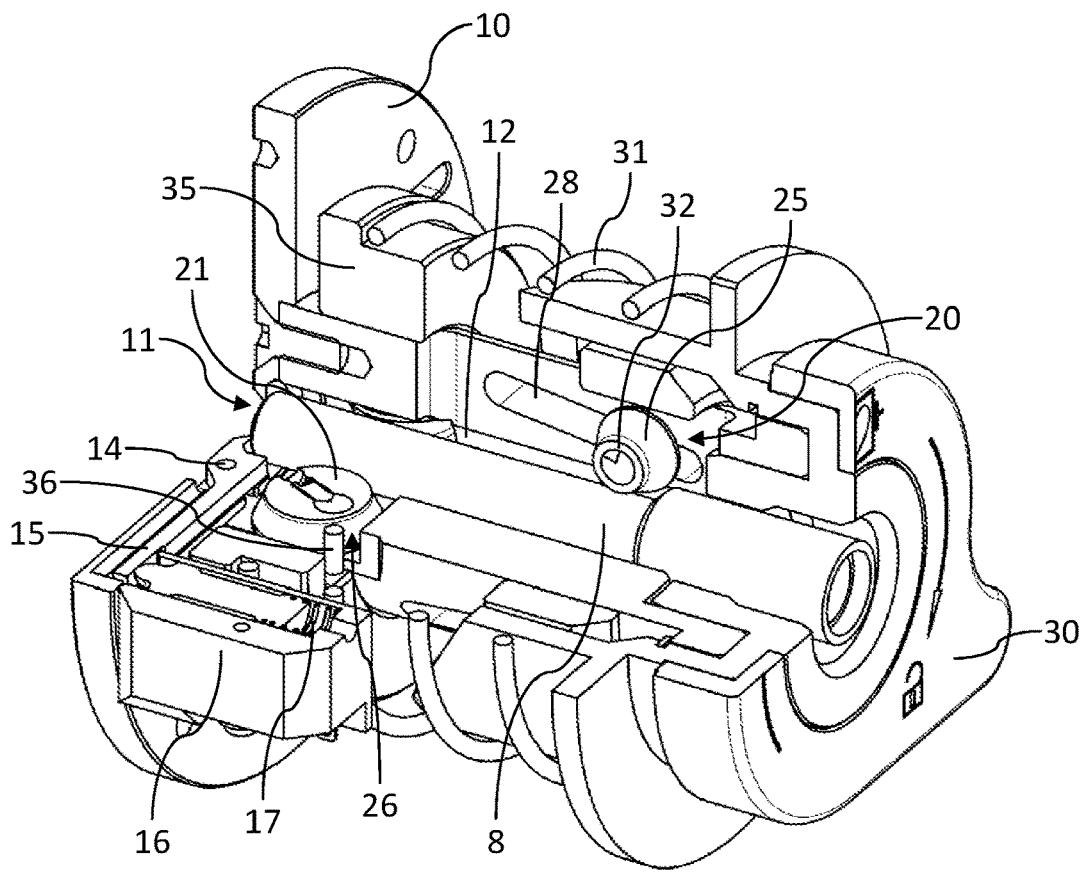
Figure 7:
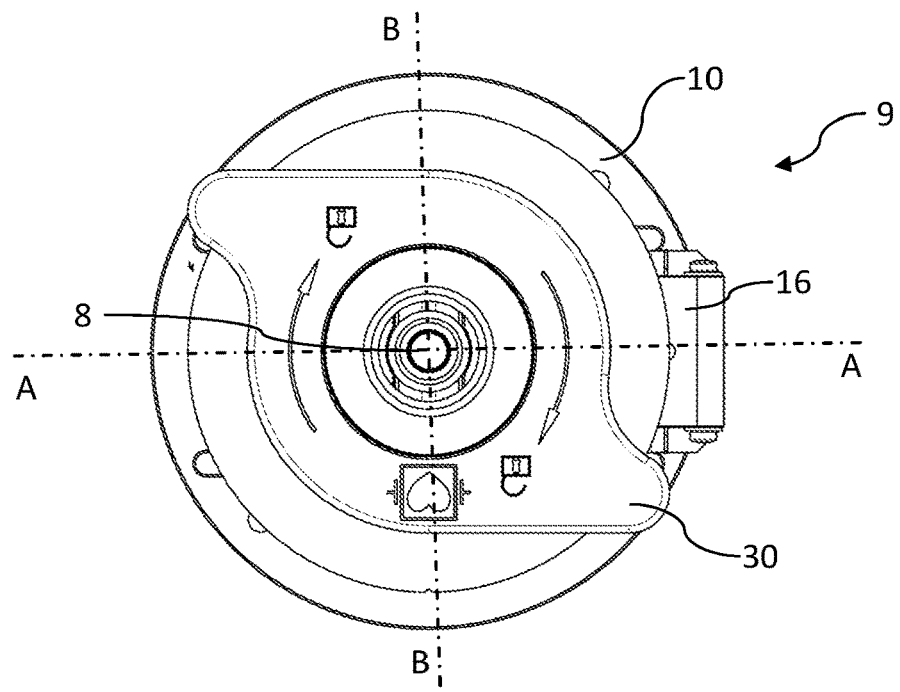
FIG. 7: shows a front view of the coupling device of FIG. 6, FIG. 8: shows a longitudinal section of the coupling device of FIG. 6 along the line A-A in FIG. 7, and FIG. 9: shows a longitudinal section of the coupling device of FIG. 6 along the line B-B in FIG. 7.
Figure 8:
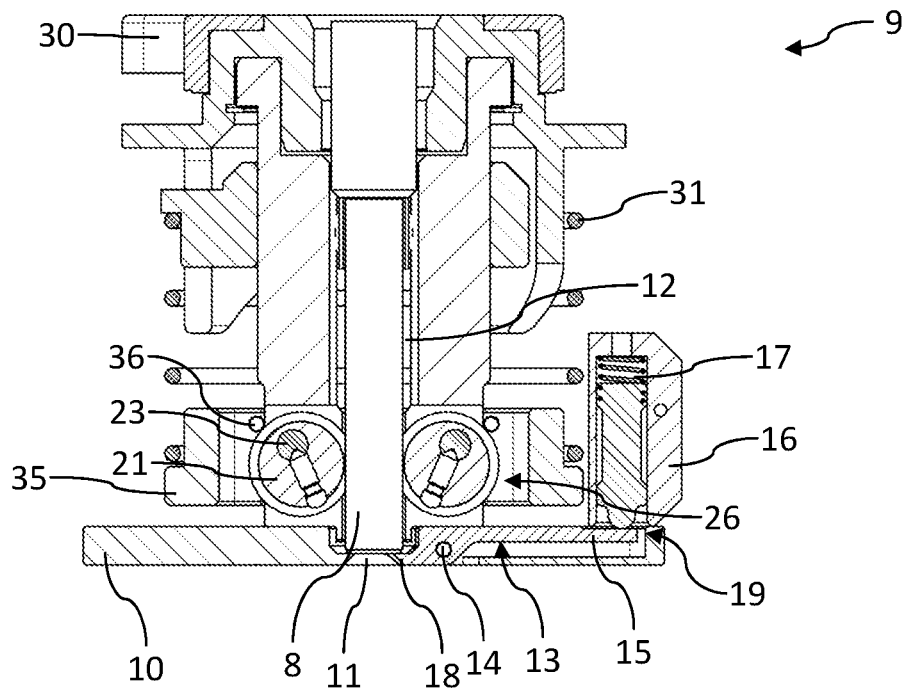
Figure 9:
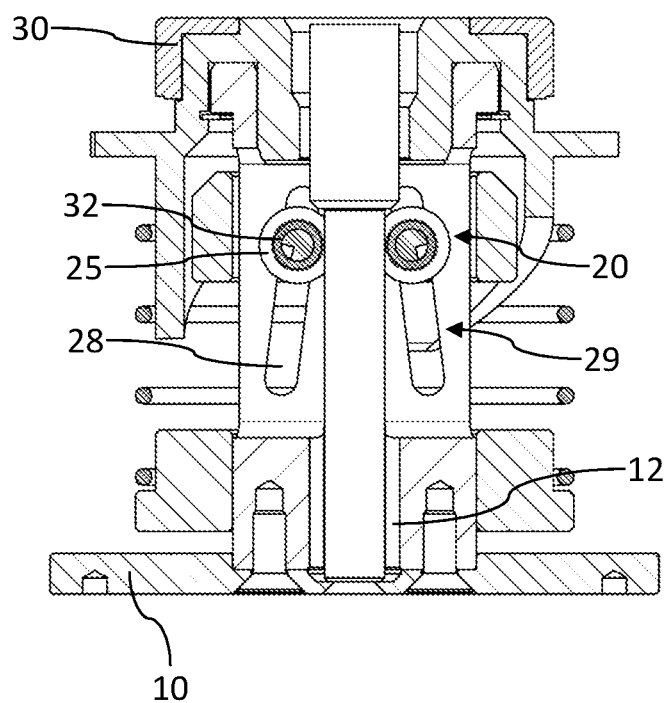

FIG. 1 schematically shows an endoscope arrangement, denoted by 1 overall, with an endoscope 2 and a light source 3.

The endoscope 2 has a rigid endoscope shaft 4 and an endoscope head 5 with an eyepiece 6 and a light-guide input 7 for feeding light. The light-guide input 7 is connected to the light source 3 by way of a light guide 8. A coupling device 9 is arranged at the light source 3, the light guide 8 being coupled to the light source 3 thereby. As a result of the coupling it is possible to use the light source 3 for light guides 8 with different diameters. Naturally, the endoscope arrangement 1 shown here only serves to elucidate the invention which cannot be construed as restricted to this example in any way. By way of example, the endoscope 2 may also have a flexible shaft and/or a video head without eyepiece, or a video shaft.

FIGS. 2 to 5 show a coupling device 9 according to a first embodiment. The coupling device 9 has a flange plate 10 by means of which said coupling device 9 can be fastened to a light source 3, for instance by screwing. A light entrance 11, through which light from the light source 3 can enter a light-guide space 12 of the coupling device 9, is arranged on the flange plate 10.

The coupling device 9 has a deactivation device 19, which is designed to electrically deactivate a light source 3. To this end, a lever 13 is arranged at the light entrance 11. The lever 13 has a pivot bearing 14 which is arranged close to the light entrance 11. As a result, a short lever arm 18, on which a light guide 8 is able to act, is formed at the light entrance 11. A switch 16 is arranged at the end of the longer lever arm 15. The lever 13 is spring loaded, for example by way of a spring 17 within the switch 16, as a result of which a rest state is defined. An inserted light guide 8 presses against the short lever arm 18. As a result, the long lever arm 15 performs a movement which actuates the switch 16. The switch 16 is electrically connected to the light source 3. The light source is configured such that the light source 3 is activated when the switch 16 is actuated, that is to say when the light guide 8 is inserted, and is deactivated without a light guide 8. The switching behavior may be defined in the light source 3, for example in a control unit. A conventional microswitch can be used as switch 16. A further advantage consists in the fact that the switching position need not be adjusted as it is predetermined by way of the geometry.

The coupling device 9 further comprises a first roller pair 20 with in each case two rollers 21. The rollers 21 of the roller pair 20 are arranged opposite one another such that a light guide 8 is located between the rollers 21.

Each roller 21 is eccentrically mounted on a respective spindle 23. Additionally, the rollers 21 each have catches 33 on the outside, said catches being connected to the spindle 23 of the rollers 21 by way of cam plates 34. Each catch 33 is guided in a respective slot 27 of a slot guide 24 and is rotatably mounted. In this case, the slots 27 are each arranged in a radial direction with respect to a light guide 8 such that the rollers 21 can be moved toward a light guide 8, and away therefrom. The catches 33 of the opposing rollers 21 are interconnected on both sides by way of a respective tension spring 22. In this way, the rollers 21 are radially displaceable and rotatable within the slot guide 24. The rollers 21 are pressed together and preloaded by way of the spring 22. This means that an inserted light guide 8 is centered as a result.

As a result of the eccentric mount of the catches 33, a rotation of a roller 21 brings about an axial movement of the slot guide 24. As a result, the catch 33 of the respective other roller 21 is forced to move axially along and brings about a rotation movement on the associated roller 21 as a result thereof.

By way of this coupling by way of the slot guide 24, a rotation of one roller 21 is necessarily transferred to the respective other roller 21 of the roller pair 20. This ensures that the position of the eccentric rollers 21 of the roller pair 20 is respectively the same in relation to a light guide 8, and hence there is accurate centration of said light guide.

The rollers 21 each have a guide groove 25 which brings about a centration of a light guide 8 transversely to the spindle 23. In this context, the guide groove 25 can be pointy or, as imaged, adapted in terms of its contour to a round light guide 8.

When a light guide 8 is inserted into the light guide space 12, the rollers 21 are pressed apart by way of a pivot movement to the diameter of the light guide 8 by said light guide. In the process, the light guide 8 is clamped by the spring force of the tension springs 22. Moreover, the light guide 8 is reliably fixated by the self-locking properties of the eccentric rollers 21. Self-locking is brought about by virtue of the rollers 21 being rotated during the withdrawal of the light guide 8, as a result of which the radius of the point of contact between rollers 21 and light guides 8, and hence the clamping force, increases.

To release the light guide 8, the coupling device 9 has a rotary actuator 30 which moves a slider in the axial direction by way of an increase. The slider acts on the cam plates 34 in the style of a slotted guide so that these cam plates are moved in the axial direction, leading to the rollers 21 being rotated and moving away from the light guide 8. The coupling device 9 has compression springs 31 which ensure the resetting of the rotary actuator 30. Thus, the compression springs 31 ensure that the rotary actuator 30 remains in its home position, even if a light guide 8 is inserted.

The coupling device 9 may have a further switch (not shown) in the region of the rotary actuator 30. In this context, the switch is triggered in the home position of the rotary actuator 30, for example by a switching cam on the rotary actuator 30. This renders it possible to identify whether a detachment process for a light guide 8 has been triggered. By way of example, this already allows a light source 3 to be deactivated even though a light guide 8 still is inserted to such an extent that the deactivation device 19 does not switch yet.

The coupling device 9 has a second roller pair 26, which has an identical design to the first roller pair 20. However, the second roller pair 26 is rotated through 90° in relation to the first roller pair 20 and is arranged closer to the light entrance 11. The slider likewise acts on the second roller pair 26, and so both roller pairs are released simultaneously.

FIGS. 6 to 9 show an alternative, second embodiment. In this embodiment, the first roller pair 20 has rollers 32 with a centric mount. Moreover, the coupling device 9 has a slotted guide 29 which has oblique slots 28, in which the rollers 32 are mounted. As a result, an axial movement of the slotted guide 29 brings about a radial movement of the rollers, either toward or away from a light guide 8. A roller pair 20 with such a slotted guide 29 is known from the prior art, which is why the function is not discussed in any more detail here.

By contrast, the combination with a second roller pair 26 with eccentrically mounted rollers 21 is novel. This second roller pair 26 has an identical or similar form to the second roller pair 26 in FIGS. 2 to 5. However, the rollers 21 of the second roller pair 26 do not have a self-locking embodiment in the example shown, and so these only center, and do not clamp, the light guide. Clamping is brought about purely by the first, centrically mounted roller pair 20. The rollers 21 of the second roller pair 26 are preloaded and centered by a ring 35 (see FIG. 6) and pins 36 inserted therein. In this case, the pins 36 are seated on the surface of the rollers 21 such that an axial movement of the pins 36 brings about a rotational movement of the rollers 21. In this way, the two rollers 21 are also coupled in terms of their rotational movement, and so a rotation of a roller 21 brings about an axial movement of the ring 35 and, moreover, a rotation of the other roller 21 of the same roller pair 26.

The ring 35 is connected to the rotary actuator 30 and the trigger mechanism of the first roller pair 20 by way of a compression spring 31. Consequently, the rollers 21 are preloaded by way of the compression spring 31.

In this case, too, the rollers 21 are rotated through 90° in relation to the rollers 32 of the first roller pair 20. Overall, this therefore yields a precise centration of a light guide 8. The centration by way of the second roller pair 26 with non-self-locking, eccentric rollers 21 is substantially simpler and more cost-effectively producible when compared to known centration devices.

What is common to both embodiments is that tilting or slipping of the light guide 8 in relation to the light entrance 11 is reduced or prevented as a result of mounting said light guide at two points.

Moreover, the structural outlay in relation to known centration devices is reduced, and so the construction of the coupling device can be implemented more easily and hence more cost-effectively.

LIST OF REFERENCE SIGNS

1 Endoscope arrangement
2 Endoscope
3 Light source
4 Endoscope shaft
5 Endoscope head
6 Eyepiece
7 Light-guide input
8 Light guide
9 Coupling device
10 Flange plate
11 Light entrance
12 Light-guide space
13 Lever
14 Pivot bearing
15 Long lever arm
16 Switch
17 Spring
18 Short lever arm
19 Deactivation device
20 First roller pair
21 Roller (eccentrically mounted)
22 Tension spring
23 Spindle
24 Slot guide
25 Guide groove
26 Second roller pair
27 Radial slot
28 Oblique slots
29 Slotted guide
30 Rotary actuator
31 Compression spring
32 Roller (centrically mounted)
33 Catch
34 Cam plates
35 Ring
36 Pins

The invention claimed is:
1. A coupling device (9) for light guides (8), comprising:
a light entrance (11);
a light-guide space (12) aligned at the light entrance (11);
a clamping device with a first roller pair (20) with two opposing rollers (21; 32), between which an inserted one of the light guides (8) is adapted to be clamped;
a second roller pair (26) with two opposing rollers (21), the second roller pair (26) being arranged closer to the light entrance (11) than the first roller pair (20), and
the rollers (21) of at least one of the first or second roller pairs (20, 26) are mounted eccentrically with a slope of less than 7°.

2. The coupling device (9) as claimed in claim 1, wherein spindles (23) of the rollers (21; 32) of the first roller pair (20) and spindles (23) of the rollers (21) of the second roller pair (26) form an angle relative to one another.

3. The coupling device (9) as claimed in claim 1, wherein the rollers (21; 32) of the first and second roller pairs (20) have a rotationally symmetric form.

4. The coupling device (9) as claimed in claim 1 wherein the rollers (21; 32) each have a for a light guide (8).

5. The coupling device (9) as claimed in claim 1, wherein the rollers (32) of one of the roller pairs (20, 26) are movable toward one another.

6. The coupling device (9) as claimed in claim 1, wherein the coupling device (9) has a guide (24) which moves the rollers (21; 32) of at least one of the roller pairs (20, 26) away from the light guide (8).

7. The coupling device (9) as claimed in claim 6, wherein the guide (24) is a slotted guide.

8. The coupling device (9) as claimed in claim 6, wherein the guide (24) has a holding position and is impinged by a spring (31) which moves the guide (24) from the holding position to an open position.

9. The coupling device (9) as claimed in claim 6, wherein the guide (24) is axially movable, and an axial movement of the guide (24) brings about a radial movement of the rollers (21; 32) of at least one of the roller pairs (20, 26).

10. The coupling device (9) as claimed in claim 6, further comprising a rotary actuator (30) and a converter, a rotational movement of the rotary actuator (30) being converted into an axial movement of the guide (24) by the converter.

11. The coupling device (9) as claimed in claim 1, wherein the rollers (21) of at least one of the roller pairs (20, 26) are self-locking.

12. The coupling device (9) as claimed in claim 1, wherein the rollers (21) of at least one of the roller pairs (20, 26) have coupled rotational movement.

13. The coupling device (9) as claimed in claim 1, wherein the rollers (21; 32) of at least one of the roller pairs (20, 26) are braced against one another by a spring (22).

14. The coupling device (9) as claimed in claim 1, further comprising a deactivation device (19) which prevents an entry of light into the light-guide space (12) when no light guide (8) has been inserted.

15. The coupling device (9) as claimed in claim 14, wherein the deactivation device electrically deactivates a light source (3).

16. The coupling device of claim 1, wherein a light guiding path of the light guides is interruptible via the light entrance (11) being closeable in light-tight fashion.

\* \* \* \* \*